(12) United States Patent
Kurkcu et al.

(10) Patent No.: US 7,721,607 B2
(45) Date of Patent: May 25, 2010

(54) ULTRASONIC INSPECTION SYSTEM, METHOD, AND APPARATUS

(75) Inventors: Nihat Kurkcu, Istanbul (TR); Oleksandr Golyk, Kocaeli (TR); Ugur Tezcan, Istanbul (TR); Ayse Kandemir, Istanbul (TR)

(73) Assignee: General Electric Company, Schenectady, NY (US)

( * ) Notice: Subject to any disclaimer, the term of this patent is extended or adjusted under 35 U.S.C. 154(b) by 100 days.

(21) Appl. No.: 11/606,745

(22) Filed: Nov. 30, 2006

(65) Prior Publication Data

US 2008/0127733 A1 Jun. 5, 2008

(51) Int. Cl.
*G01N 9/24* (2006.01)
*G01M 19/00* (2006.01)
(52) U.S. Cl. ........................ 73/643; 73/865.8
(58) Field of Classification Search ............... 73/643, 73/865.8
See application file for complete search history.

(56) References Cited

U.S. PATENT DOCUMENTS 3,107,521 A * 10/1963 McClure ............... 73/640
5,320,106 A * 6/1994 Tanaka ................. 600/466

FOREIGN PATENT DOCUMENTS

WO   WO 9709614 A1 *  3/1997

* cited by examiner

*Primary Examiner*—Hezron Williams
*Assistant Examiner*—Tamiko D Bellamy
(74) *Attorney, Agent, or Firm*—Marcella R. Louke; William Scott Andes

(57) ABSTRACT

Ultrasonic inspection system, method, and apparatus for subsurface ultrasonic inspection of curved objects. The inspection system includes an apparatus having a support structure for supporting a selected transducer and a selected acoustic mirror adapted for immersion in a coupling fluid. The total inspection path distance for the ultrasonic radiation includes a first portion defined by the transducer-to-mirror distance, and a second portion including the mirror-to-object distance. The first and second portions may be relatively adjusted within a constant total inspection path distance to focus the ultrasonic radiation at a desired subsurface depth. Selection of the transducer is at least partly dependent on subsurface depth of the desired inspection zone. Selection of the acoustic mirror is at least partly dependent on the selected transducer, the total inspection path distance, and curvature of the inspection object.

12 Claims, 3 Drawing Sheets

ULTRASONIC INSPECTION SYSTEM, METHOD, AND APPARATUS

BACKGROUND OF THE INVENTION

The present invention relates generally to ultrasonic inspection systems, and more particularly to an ultrasonic inspection apparatus including an acoustic mirror and to methods for ultrasonic inspection of parts having curved surfaces.

Ultrasonic inspection may be used to detect defects inside an object when the defects are located beneath the exterior surface. When an ultrasonic inspection is performed, a transducer is calibrated on a block having a planar entry surface (i.e., flat-top block) made from the same material as that being inspected, and containing flat bottomed holes of known diameter and known depth from the surface. A set of inspection parameters, such as gain, operating frequency, and waterpath, are set and calibrated to the flat-top block. The inspection parameters are used to inspect production hardware.

Conventionally, curved surface parts with surface curvature larger than about 38 cm radius are inspected like parts having planar surfaces. For radii less than 38 cm, typically the operator will increase the gain (energy level) in an effort to compensate for losses due to the curved entry surface. Increasing the gain, however, also increases both the system noise (electronic noise) and the material noise. Thus, some production parts become uninspectable because of "high noise." Because the ultrasound beams can be de-focused or over-focused by curved entry surfaces, the problem is escalated during subsurface inspection.

U.S. Pat. No. 6,253,619 discloses an ultrasonic inspection system that utilizes a transducer to emit ultrasonic radiation that is shaped and reflected by an adjustable acoustic mirror. U.S. Pat. No. 6,237,419 discloses an aspherical curved element transducer to inspect a part with a curved entry surface. These disclosed systems and methods do not provide desired outcomes for subsurface inspection of parts having curved entry surfaces.

Improving ultrasonic inspection capabilities through curved surfaces is desired in the art. Scientists and engineers continue to seek improved ultrasonic inspection systems and methods for inspection through curved surfaces that imitate the inspection sensitivities of inspection through a planar entry surface.

BRIEF DESCRIPTION OF THE INVENTION

The above-mentioned needs may be met by exemplary embodiments providing ultrasonic inspection systems, apparatuses, and methods. For example, an exemplary embodiment provides an inspection system comprising an apparatus having a support structure, a mirror holder, and a selectively replaceable acoustic mirror selected from a plurality of acoustic mirrors. The support structure is adapted for supporting a selected transducer in a transducer holder. The selected acoustic mirror is operable to shape and reflect ultrasonic radiation generated by the selected transducer. At least one of the transducer and the acoustic mirror are mounted in movable relationship with the support structure wherein a transducer-to-mirror distance is adjustable.

An exemplary embodiment provides an apparatus comprising a support structure, a mirror holder, and a selectively replaceable acoustic mirror selected from a plurality of acoustic mirrors. The support structure is adapted for supporting a selected transducer and the selected acoustic mirror such that a transducer-to-mirror distance is adjustable.

An exemplary embodiment includes an ultrasonic inspection method. The exemplary method includes selecting a transducer from a plurality of transducers, wherein selection of the transducer is at least partially dependent on a depth of a first zone of a first inspection object to be inspected. The exemplary method includes mounting the selected transducer in supporting connection with a support structure. The exemplary method includes selecting an acoustic mirror from a plurality of acoustic mirrors, wherein selection of the acoustic mirror is at least partially dependent on an entry surface curvature of the first inspection object. The selected acoustic mirror is mounted in supporting connection with the support structure, wherein the selected transducer and the selected acoustic mirror are disposed an initial transducer-to-mirror distance. The transducer-to-mirror distance is adjustable and defines a first portion of a predetermined constant total inspection path distance. The method includes shaping and reflecting ultrasonic radiation generated by the selected transducer with the selected acoustic mirror toward the first zone. In an exemplary method, the first portion, i.e., the transducer-to-mirror distance, is adjusted within the constant total inspection path distance.

BRIEF DESCRIPTION OF THE DRAWINGS

The accompanying drawings illustrate an embodiment of the invention wherein.

DETAILED DESCRIPTION OF THE INVENTION

Figure 1:
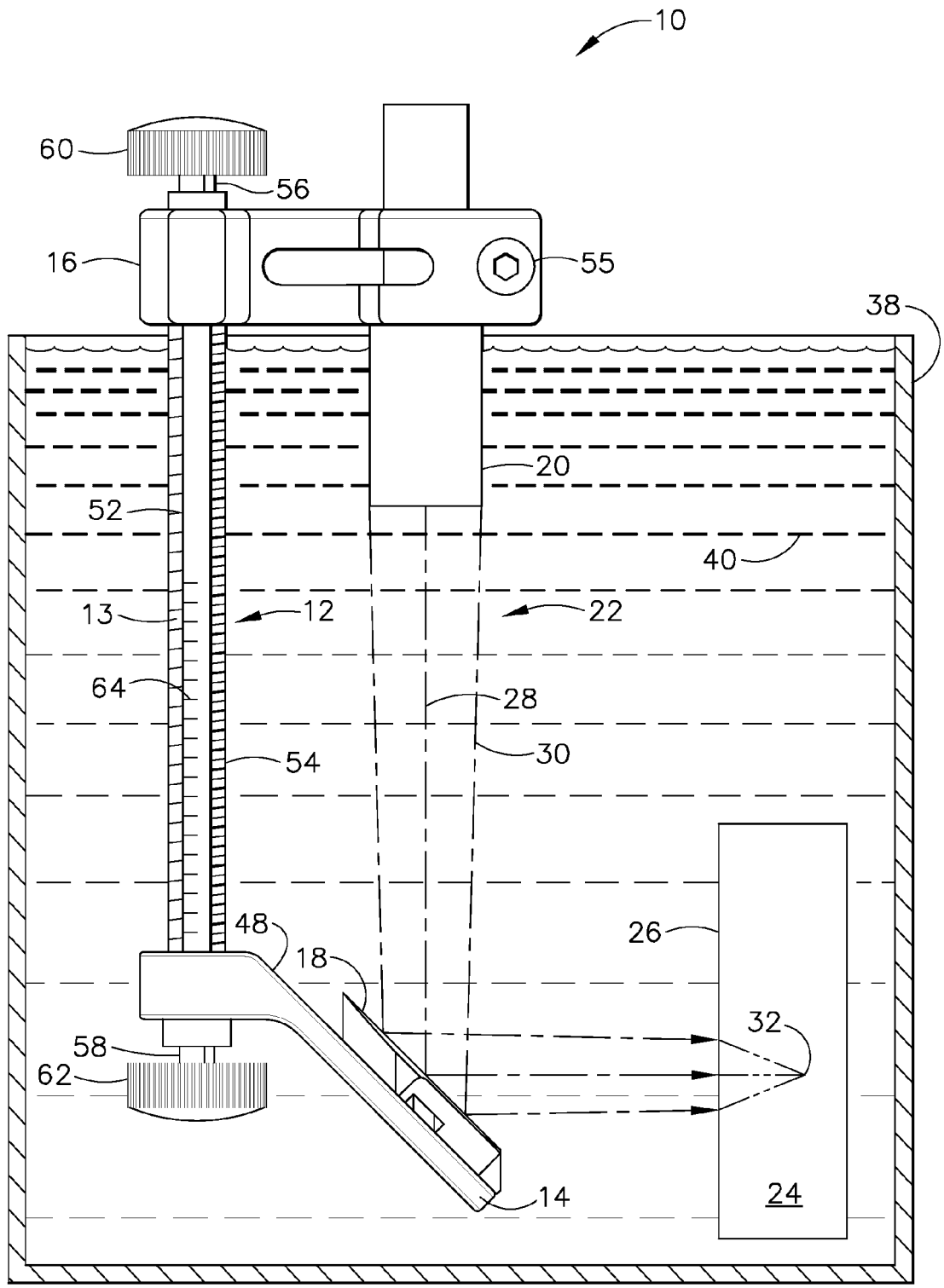
FIG. 1 is a side elevation of an embodiment of an ultrasonic inspection system.
Figure 2:
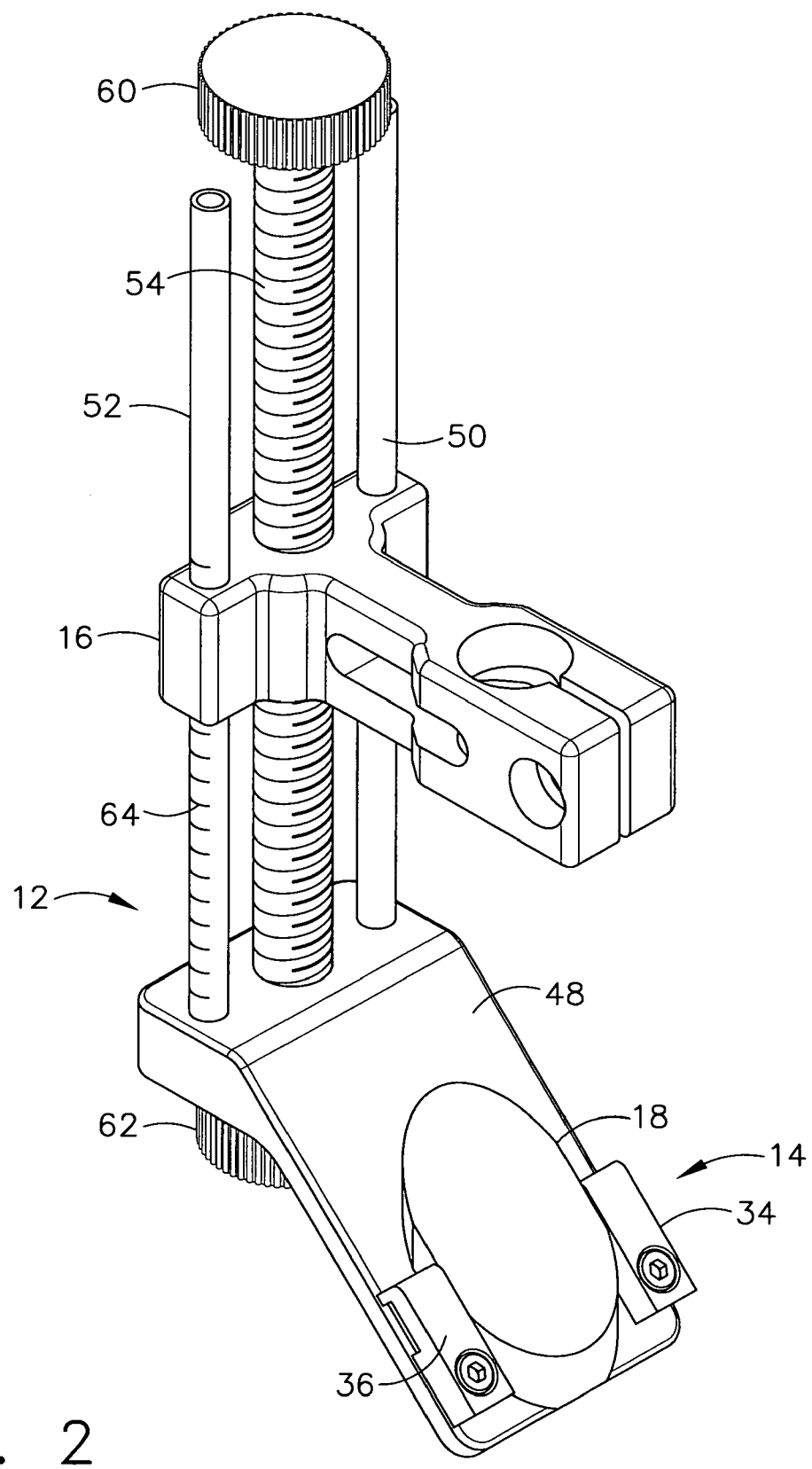
FIG. 2 is an isometric view of a support structure having an acoustic mirror mounted thereto.
Figure 3:
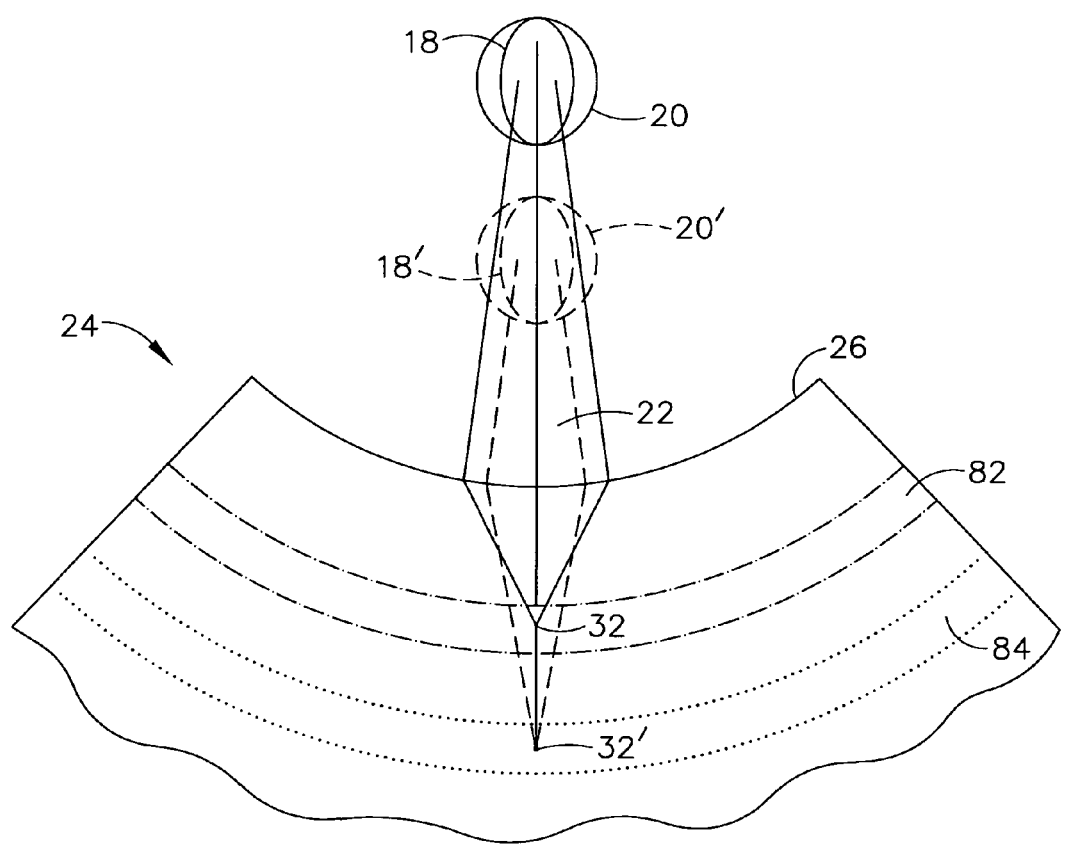
FIG. 3 is a schematic representation of an ultrasonic inspection of an object having a curved entry surface, where inspection is made at two subsurface zones of the inspection object.

Referring now to the drawings, FIGS. 1-3 disclose exemplary embodiments wherein an ultrasonic inspection system 10 includes an exemplary apparatus 12 having a support structure 13. Apparatus 12 includes a mirror holder 14 and a transducer holder 16. The mirror holder 14 is adapted to secure a curved acoustic mirror 18 to support structure 13. The transducer holder 16 is adapted to hold a transducer 20. In an exemplary embodiment, the acoustic mirror 18 and the transducer 20 are separated by a transducer-to-mirror distance and are disposed so that ultrasonic radiation 22 emitted by the transducer 20 is shaped and reflected by acoustic mirror 18 toward an object 24. Object 24 may include a curved entry surface 26 which may be substantially convex or concave, depending on the particular application. In an exemplary embodiment, the transducer-to-mirror distance is adjustable. In an exemplary embodiment, the acoustic mirror 18 and transducer 20 are disposable in an immersion tank 38 which holds coupling fluid 40.

The exemplary apparatus 12 includes mirror holder 14 and transducer holder 16. Two guide rods 50, 52 extend from the mirror holder to support and guide the transducer holder 16. A threaded rod 54, having a first end 56 and a second end 58, is disposed between the guide rods 50, 52. In an exemplary embodiment, transducer holder 16 is operationally engaged with threaded rod 54. A first knob 60 is operationally attached to first end 56. Likewise, a second knob 62 is operationally attached to second end 58. Rotation of first knob 60 or second knob 62 rotates threaded rod 54, which in turn causes translational movement of the transducer holder 16. In other exemplary embodiments, mirror holder 14 may be movable responsive to rotation of the threaded rod 54. During an inspection operation, movement of the transducer holder 16, or the mirror holder 14, or both, along the axis of threaded rod 54 provides for an adjustable transducer-to-mirror distance.

In an exemplary embodiment, at least one of the guide rods (i.e., guide rod 52) includes measurement delineations 64 to allow visual perception of the separation of the mirror holder 14 and the transducer holder 16. As is readily appreciated, when a transducer 20 is in the transducer holder 16 and an acoustic mirror 18 occupies the mirror holder 14, the measurement delineations 64 may be utilized to visually perceive a transducer-to-mirror distance.

With particular reference to FIG. 2, in an exemplary embodiment, the mirror holder 14 includes an attachment device, such as a pair of clips 34, 36 that allow easy replacement of acoustic mirror 18 with another acoustic mirror. In an exemplary embodiment, acoustic mirror 18 may be a convex acoustic mirror or a concave acoustic mirror depending on the particular application. In an exemplary embodiment, acoustic mirror 18 represents a plurality of acoustic mirrors including at least one of a concave acoustic mirror and a convex acoustic mirror. In an exemplary embodiment, clips 34 and 36 are designed so that mirror 18 can be attached manually, without the need for extraneous tools. Thus, replacement of a first acoustic mirror with a second acoustic mirror can be readily achieved.

In an exemplary embodiment, the mirror holder 14 includes a support surface 48 which may be aligned at an angle of substantially forty-five degrees with respect to an axis of the threaded rod 54.

In an exemplary inspection system, the transducer 20, the acoustic mirror 18, and the inspection object 24 are disposed in an immersion tank 38 containing a coupling fluid 40. The acoustic mirror 18 and inspection object 24 are separated by a mirror-to-object distance. A total inspection path distance includes a first portion and a second portion. The first portion is defined by the transducer-to-mirror distance. A mirror-to-object distance extends at least from the acoustic mirror 18 to the inspection object 24 and defines the second portion of the total inspection path distance. In an exemplary embodiment, as explained in greater detail below, for a particular subsurface inspection, the total inspection path distance is held constant and the transducer-to-mirror distance and the mirror-to-object distance are relatively adjusted to focus the ultrasonic radiation within the desired inspection zone. The total inspection path distance may be predetermined in a calibration process.

In an exemplary embodiment, the acoustic mirror 18 is selected from a plurality of acoustic mirrors. The plurality of acoustic mirrors includes mirrors having differing radii of curvature. The plurality of acoustic mirrors may include concave mirrors and convex mirrors. Selection of the acoustic mirror 18 for the particular subsurface inspection is at least partly dependent on the radius of curvature of the inspection object 24. Other factors influencing mirror selection may include depth of the desired inspection zone, velocity of sound in the material, diameter and/or focal length of the selected transducer. An exemplary inspection system includes an algorithm operable to determine the mirror radius based on selected inputs.

In an exemplary inspection system, as illustrated in FIG. 3, the inspection object 24 may include more than one inspection zone, i.e., zones 82, 84. The first inspection zone 82 is associated with a first total inspection path distance. The second inspection zone 84 is associated with a second total inspection path distance. Inspection of different zones 82, 84 in the same inspection object 24 may require selection of a different transducer, i.e., transducer 20', a different acoustic mirror, i.e., mirror 18', or both.

An exemplary embodiment provides a method that includes selecting a transducer 20 from a plurality of transducers. The selection of the transducer is at least partly dependent on a depth of a first inspection zone of an inspection object 24. Table 1 below provides guidance as to selection of a transducer with respect to subsurface depth of inspection zones.

TABLE 1

| | Inspection Area | Transducer | | |
|---|---|---|---|---|
| Zone | (Sub-surface depth) in. (mm) | f (MHz) | F in. (mm) | d in. (mm) |
| 1 | 0.4-1.1 (10.2-27.9) | 10 | 6 (152) | 0.75 (19.1) |
| | | | 8 (203) | 1 (25.4) |
| 2 | 0.9-1.6 (22.9-40.6) | 10 | 6 (152) | 0.75 (19.1) |
| | | | 8 (203) | 1 (25.4) |
| 3 | 1.4-2.1 (35.6-53.3) | 10 | 8 (203) | 1 (25.4) |
| | | | 10 (254) | 1 (25.4) |
| 4 | 1.9-2.6 (48.3-66.0) | 10 | 10 (254) | 1 (25.4) |
| 5 | 2.4-3.6 (61.0-91.4) | 10 | 13 (330) | 1 (25.4) |
| 6 | 3.4-5.6 (86.4-142.2) | 10 | 16 (406) | 1 (25.4) |

The selected transducer 20 is mounted in supporting connection with the support structure 13 in the transducer holder 16. An acoustic mirror 18 is selected from a plurality of acoustic mirrors. In an exemplary embodiment, the selection of the first acoustic mirror 18 is at least partly dependent on the radius of curvature of the object to be ultrasonically inspected, depth of focus, material sound velocity, transducer diameter, and transducer focal length. In an exemplary embodiment, an algorithm is operable to determine the mirror radius based on inputs such as focal length and diameter of the selected transducer, the total inspection path distance (determined during calibration), curvature type and radius of the inspection object, and sound velocity in the coupling fluid and in the object material.

With reference again to FIGS. 1 and 2, the selected acoustic mirror 18 is mounted in supporting connection with the support structure 13 at an initial transducer-to-mirror distance. The acoustic mirror 18 is disposed so that radiation generated by transducer 20 is shaped and reflected toward an inspection object 24 by acoustic mirror 18. In an exemplary embodiment, mirror 18 is disposed generally 45° to an axis of the support structure 13. In an exemplary embodiment, the angle of the acoustic mirror 18 is substantially constant, however, it is within the scope of the disclosure to include a mirror holder 14 that is operable to adjust the mirror angle according to the particular application.

Ultrasonic radiation generated by transducer 20 is received by acoustic mirror 18 and is shaped and reflected toward an inspection object 24. The shaped/reflected radiation passes through the curved entry surface 26 and is focused at a focal point 32. In an exemplary embodiment, focal point 32 coincides with the desired inspection zone. In an exemplary embodiment, the depth of inspection zone can be changed depending on the mirror radius.

For example, as illustrated in FIG. 3, acoustic mirror 18 operates to reflect and shape the ultrasonic radiation 22 generated by transducer 20 toward the inspection object 24. The radiation 22 is focused at a focal point 32 within the desired inspection zone 82. In an exemplary embodiment, acoustic mirror 18' may operate to reflect and shape ultrasonic radiation generated by transducer 20' toward inspection object 24.

The radiation 22 is focused at a focal point 32' within inspection zone 84. The depth of the focal points 32, 32' is at least partly dependent on the curvature of entry surface 26.

The inspection path distance from the transducer to the entry surface is determined in a calibration operation. In an exemplary method, the total inspection path distance, the selected transducer focal length and diameter, and the curvature radius of the object to be inspected are input to an algorithm that relates the information to a desired acoustic mirror radius. An acoustic mirror 18 is then selected from a plurality of acoustic mirrors. The algorithm may also provide an ideal transducer-to-mirror distance and an ideal mirror-to-object distance that represent first and second portions, respectively, of the total inspection path distance.

In an exemplary embodiment, the selected transducer 20 is engaged in supporting connection with the transducer holder 16 and the selected mirror 18 is engaged in supporting connection with the mirror holder 14. Knob 60 or knob 62 is rotated to provide the desired transducer-to-mirror distance. The support structure 13 may be placed into the immersion tank 38 so that the transducer 20 and mirror 18 are disposed within the coupling fluid 40. The support structure 13 is manipulated so as to provide the desired mirror-to-object distance. Ultrasonic radiation generated by the transducer is then shaped and reflected by the acoustic mirror toward the desired zone of the object to be inspected. Knob 60 may be adjusted to fine tune focusing of the ultrasonic radiation in the desired inspection zone.

The transducer-to-mirror distance and the mirror-to-object distance may be relatively adjusted within a constant total inspection path distance so that the ultrasonic radiation in focused at the desired depth. Thus, subsurface inspection of curved parts may be performed with substantially similar sensitivity as inspection of parts having planar entry surfaces.

While the present invention has been illustrated by a description of a method and several expressions of an embodiment, it is not the intention of the applicants to restrict or limit the spirit and scope of the appended claims to such detail. Numerous other variations, changes, and substitutions will occur to those skilled in the art without departing from the scope of the invention.

What is claimed is:

1. An inspection system comprising:
    an apparatus comprising:
        a support structure wherein the support structure is adapted for supporting a selected transducer in a transducer holder;
        a mirror holder mounted in supporting connection with the support structure;
        a selectively replaceable acoustic mirror selected from a plurality of acoustic mirrors, wherein the selected acoustic mirror is operable to shape and reflect ultrasonic radiation generated by the selected transducer, wherein the selected acoustic mirror is removably mounted in supporting relationship with the mirror holder wherein at least one of the selected transducer and the selected acoustic mirror are mounted in movable relationship with the support structure wherein a transducer-to-mirror distance is adjustable; and
    a mirror-to-object distance extending at least from the selected acoustic mirror to a first inspection object, wherein the mirror-to-object distance is adjustable, and wherein a total inspection path distance includes a first portion defined by the transducer-to-mirror distance and a second portion defined by the mirror-to-object distance.

2. The inspection system according to claim 1 wherein the total inspection path distance is a predetermined distance.

3. The inspection system according to claim 1 wherein the plurality of acoustic mirrors includes at least a first acoustic mirror generally related to an entry surface curvature of the first inspection object and a second acoustic mirror generally related to an entry surface curvature of a second inspection object.

4. The inspection system according to claim 1 wherein the first inspection object includes at least first and second inspection zones, and wherein the first inspection zone is associated with a first total inspection path distance, and wherein the second inspection zone is associated with a second total inspection path distance.

5. The inspection system according to claim 1, wherein the system further comprises:
    an algorithm relating at least two of transducer selection, entry surface curvature, total inspection path distance, acoustic mirror selection, and a velocity of ultrasonic radiation.

6. The inspection system according to claim 1, wherein the plurality of acoustic mirrors includes at least one member selected from the group consisting of a concave acoustic mirror and a convex acoustic mirror.

7. Apparatus comprising:
    a support structure wherein the support structure is adapted for supporting a selected transducer in a transducer holder;
    a mirror holder mounted in supporting connection with the support structure; and
    a selectively replaceable acoustic mirror selected from a plurality of acoustic mirrors, wherein the selected acoustic mirror is operable to shape and reflect ultrasonic radiation generated by the selected transducer, wherein the selected acoustic mirror is removably mounted in supporting relationship with the mirror holder;
    wherein at least one of the selected transducer and the selected acoustic mirror are mounted in movable relationship with the support structure wherein a transducer-to-mirror distance is adjustable.

8. A method comprising:
    selecting a transducer from a plurality of transducers, wherein selection of the transducer is at least partially dependent on a depth of a first zone to be inspected of a first inspection object;
    mounting the selected transducer in supporting connection with a support structure;
    selecting an acoustic mirror from a plurality of acoustic mirrors, wherein selection of the acoustic mirror is at least partially dependent on an entry surface curvature of the first inspection object;
    mounting the selected acoustic mirror in supporting connection with the support structure, wherein the selected transducer and the selected acoustic mirror are disposed at an initial transducer-to-mirror distance, and wherein the transducer-to-mirror distance is adjustable, and wherein the transducer-to-mirror distance defines a first portion of a predetermined constant total inspection path distance;
    shaping and reflecting ultrasonic radiation generated by the selected transducer with the selected acoustic mirror toward the first zone; and
    adjusting the transducer-to-mirror distance within the constant total inspection path distance.

9. The method according to claim 8 further comprising:
prior to (e), immersing the selected transducer and the selected acoustic mirror in a coupling fluid containing the first inspection object, wherein the first inspection object is disposed at an initial mirror-to-object distance extending at least from the selected acoustic mirror to the first inspection object, wherein the mirror-to-object distance is adjustable, and wherein the mirror-to-object distance defines a second portion of the total inspection path distance.

10. The method according to claim 9 further comprising:
adjusting the mirror-to-object distance within the constant total inspection path distance.

11. The method according to claim 10 further comprising:
selectively replacing at least one of the selected transducer with a second transducer and the selected acoustic mirror with a second acoustic mirror, wherein selection of the second transducer or the second acoustic mirror is at least partially dependent on a depth of a subsequent zone to be inspected of the first inspection object.

12. The method according to claim 9 further comprising:
selectively replacing the first inspection object with a second inspection object, wherein an entry surface curvature of the second object is different than the entry surface curvature of the first inspection object; and
selectively replacing at least one of the selected transducer with a second transducer selected from the plurality of transducers and the selected acoustic mirror with a second acoustic mirror selected from the plurality of acoustic mirrors, wherein selection of the second transducer or the second acoustic mirror is at least partially dependent on a depth of a zone to be inspected of the second inspection object.

* * * * *